US007709450B2

(12) United States Patent
Eriksson et al.

(10) Patent No.: US 7,709,450 B2
(45) Date of Patent: May 4, 2010

(54) STIMULATION OF VASCULARIZATION WITH VEGF-B-186

(75) Inventors: Ulf Eriksson, Stockholm (SE); Xuri Li, Stockholm (SE); Peter Carmeliet, Zwijnaarde (BE); Desire Collen, Zwijnaarde (BE)

(73) Assignees: Ludwig Institute for Cancer Research, New York, NY (US); Flanders Interuniversity Institute for Biotechnology, Zwijnaarde (BE)

( * ) Notice: Subject to any disclaimer, the term of this patent is extended or adjusted under 35 U.S.C. 154(b) by 812 days.

(21) Appl. No.: 10/175,153

(22) Filed: Jun. 20, 2002

(65) Prior Publication Data

US 2003/0008824 A1    Jan. 9, 2003

Related U.S. Application Data

(60) Provisional application No. 60/299,192, filed on Jun. 20, 2001.

(51) Int. Cl.
*A61K 31/70*    (2006.01)

(52) U.S. Cl. .................................................. 514/44

(58) Field of Classification Search ............... 514/44, 514/2–21; 435/320.1; 424/198.1
See application file for complete search history.

(56) References Cited

U.S. PATENT DOCUMENTS

| 5,607,918 | A | | 3/1997 | Eriksson et al. |
| 5,840,693 | A | | 11/1998 | Eriksson et al. |
| 5,928,939 | A | * | 7/1999 | Eriksson et al. ............ 435/325 |
| 6,121,246 | A | * | 9/2000 | Isner ........................... 514/44 |
| 6,793,918 | B2 | * | 9/2004 | Enholm et al. ............. 424/93.2 |

FOREIGN PATENT DOCUMENTS

| WO | WO 98/19300 A | 5/1998 |
| WO | WO 98/49300 A | 11/1998 |
| WO | WO 00/52462 A | 9/2000 |
| WO | WO 00/64261 A | 11/2000 |

OTHER PUBLICATIONS

Anderson (Nature 1998; 392(suppl):25-30).*
Dang et al. (Clin. Cancer Res. 1999; 5:471-474).*
Green and Seymour (Cancer Gene Therapy; 2002; 9:1036-42).*
Carmeliet, P., *Mechanisms of angiogenesis and arteriogenesis.* Nat Med, 2000. 6(4): p. 389-95.
Carmeliet, P. and R.K. Jain, *Angiogenesis in cancer and other diseases.* Nature, 2000. 407(6801): p. 249-57.
Li, X. And U. Eriksson, *Novel VEGF family members: VEGF-B, VEGF-C and VEGF-D.* Int J Biochem Cell Biol, 2001. 33(4): p.421-6.
Carmeliet P, et al., *Abnormal blood vessel development and lethality in embryos lacking a single VEGF allele.* Nature, 1996. 380(6573): p. 435-9.

Ferrara N, et al., *Heterozygous embryonic lethality induced by targeted inactivation of the VEGF gene.* Nature, 1996. 380(6573): p. 439-42.
Poltorak, Z., T. Cohen, and G. Neufeld, *The VEGF splice variants: properties, receptors, and usage for the treatment of ischemic diseases.* Herz, 2000. 25(2): p. 126-9.
Carmeliet, P., *VEGF gene therapy: stimulating angiogenesis or angioma-genesis?* [In Process Citation]. Nat Med, 2000. 6(10): p. 1102-3.
Olofsson B, et al., *Vascular endothelial growth factor B, a novel growth factor for endothelial cells.* Proceedings of the National Academy of Sciences of the United States of America, 1996. 93(6): p. 2576-81.
Grimmond S, et al., *Cloning and characterization of a novel human gene related to vascular endothelial growth factor.* Genome Research, 1996. 6(2): p. 124-31.
Olofsson B, et al., *Vascular Endothelial Growth Factor B (VEGF-B) Binds to VEGF Receptor-1 and Regulates Plasminogen Activator Activity in Endothelial Cells.* Proceedings of the National Academy of Sciences of the United States of America, 1998. 95(20): p. 11709-11714.
Soker, S., *Neuropilin in the midst of cell migration and retraction.* Int J Biochem Cell Biol, 2001. 33(4): p. 433-7.
Aase K, et al., *Localization of VEGF-B in the mouse embryo suggests a paracrine role of the growth factor in the developing vasculature,* Developmental Dynamics, 1999, 215(1): p. 12-25.
Makinen T, et al., *Differential binding of vascular endothelial growth factor B splice and proteolytic isoforms to neuropilin-1.* Journal of Biological Chemistry, 1999. 274(30): p. 21217-21222.
Kitsukawa T, et al., *Overexpression of a membrane protein, neuropilin, in chimeric mice causes anomalies in the cardiovascular system, nervous system and limbs.* Development, 1995. 121(12): p. 4309-18.
Ikuta, T., H. Ariga, and K. Matsumoto, *Extracellular matrix tenascin-X in combination with vascular endothelial growth factor B enhances endothelial cell proliferation.* Genes Cells, 2000. 5(11): p. 913-927.
Bellomo D, et al., *Mice lacking the vascular endothelial growth factor-B gene (VEGFB) have smaller hearts, dysfunctional coronary vasculature, and impaired recovery from cardiac ischemia.* Circulation Research, 2000. 86(2): p. E29-E35.
Gunningham, S.P., et al., *VEGF-B expression in human primary breast cancers is associated with lymph node metastasis but not angiogenesis.* J Pathol, 2001. 193(3): p. 325-32.
Andre, T., et al., *VEGF, VEGF-B, VEGF-C and their receptors KDR, FLT-1 and FLT-4 during the neoplastic progression of human colonic mucosa.* Int J Cancer, 2000. 86(2): p. 174-81.
Eggert, A., et al., *High-level expression of angiogenic factors is associated with advanced tumor stage in human neuroblastomas* [in Process Citation]. Clin Cancer Res, 2000. 6(5): p. 1900-8.

(Continued)

*Primary Examiner*—J. E Angell
(74) *Attorney, Agent, or Firm*—Crowell & Moring LLP (57) ABSTRACT

VEGF-B is shown to be needed for cardiac muscle revascularization after heart infarction, and methods of promoting or stimulating vascular development, e.g. angiogenesis and/or arteriogenesis, particularly in ischemic mammals, are disclosed.

11 Claims, 3 Drawing Sheets

OTHER PUBLICATIONS

Niki, T., et al., *Expression of vascular endothelial growth factors A, B, C, and D and their relationships to lymph node status in lung adenocarcinoma [in Process Citation]*. Clin Cancer Res, 2000. 6(6): p. 2431-9.

Salven P, et al., *Vascular Endothelial Growth Factors VEGF-B and VEGF-C Are Expressed in Human Tumors*. American Journal of Pathology, 1998. 153(1): p. 103-108.

Sowter Hm, et al., *Expression and Localization Of the Vascular Endothelial Growth Factor Family in Ovarian Epithelial Tumors*. Laboratory Investigation, 1997. 77(6): p. 607-614.

Gunningham, S.P., et al., *Vascular endothelial growth factor-B and vascular endothelial growth factor-C expression in renal cell carcinomas: regulation by the von Hippel-Lindau gene and hypoxia*. Cancer Res, 2001. 61(7): p. 3206-11.

Heymans S, et al., *Inhibition of plasminogen activators or matrix metalloproteinases prevents cardiac rupture but impairs therapeutic angiogenesis and causes cardiac failure*. Nature Medicine, 1999. 5(10): p. 1135-1142.

Dalrymple-Hay, M.J., et al., *Postinfarction ventricular septal rupture: the Wessex experience*. Semin Thorac Cardiovasc Surg, 1998. 10(2): p. 111-6.

Varbella, F., et al., Subacute left ventricular free-wall rupture in early course of acute myocardial infarction. Clinical report of two cases and review of the literature. G Ital Cardiol, 1999. 29(2): p. 163-70.

Bellomo D et al: "Mice Lacking the Vascular Endothelial Growth Factor-Beta Gene (VEGFB) Have Smaller Hearts, Dysfunctional Coronary Vasculature and Impaired Recovery From Cardiac Ischemia" Circulation Research, Grune and Stratton, Baltimore, US, vol. 86, No. 2, E29-E35, XP0010906239, Feb. 4, 2000.

European Search Report Dated Sep. 27, 2005 (Three (3) Pages).

Zxu J. et al.: "Dobutamine stress experiment study on porcine chronic ischemic myocardlum before and after gene transfer by ultrasonic integrated backscatter" Zongguo Chaosheng Yixue Zazhi vol. 19, No. 6, 2003, pp. 405-409.

Supplementary European Search Report Dated Nov. 2, 2005.

European Search Report Dated Dec. 6, 2005.

Abraham et al., *Transplantation*, vol. 73, 1703-1706, No. 11, Jun. 15, 2002.

* cited by examiner

STIMULATION OF VASCULARIZATION WITH VEGF-B-186

CROSS REFERENCE TO RELATED APPLICATIONS

This application claims priority of U.S. provisional patent application No. 60/299,192, filed Jun. 20, 2001.

BACKGROUND OF THE INVENTION

Vasculogenesis, the de novo formation of blood vessels, and angiogenesis, the growth of new capillaries from pre-existing ones, are critical for embryonic development and normal physiological functions in adults [Carmeliet, P., *Mechanisms of angiogenesis and arteriogenesis*. Nat Med, 2000 6(4) 389-95]. Failure of these processes leads to early death of the embryo as a result of impaired formation of the vascular tree and somatic growth. In adults, abnormal angiogenesis can lead to impaired wound healing, poor tissue regeneration in ischemic conditions, cyclical growth of the female reproductive system, and tumor development [Carmeliet, P. and R. K. Jain, *Angiogenesis in cancer and other diseases*. Nature, 2000 407(6801) 249-57].

The vascular endothelial growth factor (VEGF) family of growth factors are the most important players involved in physiological and pathological angiogenesis. Thus far, five VEGF family members have been discovered, including VEGF-A, VEGF-B, VEGF-C, VEGF-D and PlGF [Li, X. and U. Eriksson, Novel VEGF family members: VEGF-B, VEGF-C and VEGF-D. Int J Biochem Cell Biol, 2001 33(4) 421-6]. Among them, VEGF-A is the most potent angiogenic factor, but it requires fine-tuned control of its expression and regulation. Lack of a single VEGF allele results in embryonic lethality [Carmeliet P, et al., *Abnormal blood vessel development and lethality in embryos lacking a single VEGF allele*. Nature, 1996 380(6573) 435-39; and Ferrara N, et al., *Heterozygous embryonic lethality induced by targeted inactivation of the VEGF gene*. Nature, 1996 380(6573) 439-42]. VEGF-A binds to four receptors, VEGFR-1, VEGFR-2, neuropilin-1 and neuropilin-2 [Poltorak, Z., T. Cohen, and G. Neufeld, The VEGF splice variants: properties, receptors, and usage for the treatment of ischemic diseases, Herz, 2000 25(2) 126-9]. Through these receptors, VEGF-A promotes endothelial cell proliferation, induces vascular permeability and chemo-attracts monocytes. VEGF-A expression is efficiently upregulated by hypoxia. The potent angiogenic capacity of VEGF-A gives it potential therapeutic utility in ischemic diseases where physiological angiogenesis is needed. However, clinical use of VEGF-A has been hampered because of its severe side effects [Carmeliet, P., *VEGF gene therapy: stimulating angiogenesis or angioma-genesis?*, Nat Med, 2000 6(10) 1102-03].

VEGF-B was the third member of the VEGF family to be discovered (after VEGF-A and VEGF-C) [Olofsson B, et al., *Vascular endothelial growth factor B, a novel growth factor for endothelial cells*. Proceedings of the National Academy of Sciences of the United States of America, 1996 93(6) 2576-81], [Grimmond S, et al., *Cloning and characterization of a novel human gene related to vascular endothelial growth factor*. Genome Research, 1996, 6(2) 124-31]. VEGF-B has similar angiogenic and other properties to those of VEGF-A, but is distributed and expressed in tissues differently from VEGF-A. In particular, VEGF-B is very strongly expressed in the heart, and only weakly in the lungs, whereas the reverse is the case for VEGF-A [Olofsson, B. et al, Proc. Natl. Acad. Sci. USA 1996 93 2576-2581]. RT-PCR assays have demonstrated the presence of VEGF-B mRNA in melanoma, normal skin, and muscle. This suggests that VEGF-A and VEGF-B, despite the fact that they are co-expressed in many tissues, have functional differences. A comparison of the PDGF/VEGF family of growth factors reveals that the 167 amino acid isoform of VEGF-B is the only family member that is completely devoid of any glycosylation. Gene targeting studies have shown that VEGF-B deficiency results in mild cardiac phenotype, and impaired coronary vasculature [Bellomo et al, Circ Res, 2000 86 E29-35].

Human VEGF-B was isolated using a yeast co-hybrid interaction trap screening technique by screening for cellular proteins which might interact with cellular retinoic acid-binding protein type I (CRABP-I). The isolation and characteristics including nucleotide and amino acid sequences for both human and murine VEGF-B are described in detail in PCT/US96/02957, in U.S. Pat. Nos. 5,840,693 and 5,607,918 by Ludwig Institute for Cancer Research and The University of Helsinki and in Olofsson et al, Proc. Natl. Acad. Sci. USA 1996 93 2576-2581. The nucleotide sequence for human VEGF-B is also found at GenBank Accession No. U48801. The entire disclosures of the International Patent Application PCT/US97/14696 (WO 98/07832), U.S. Pat. Nos. 5,840,693 and 5,607,918 are incorporated herein by reference.

The human and murine genes for VEGF-B are almost identical, and both span about 4 kb of DNA. The genes are composed of seven exons, and their exon-intron organization resembles that of the VEGF-A and PlGF genes [Grimmond et al, Genome Res, 1996 6 124-131; Olofsson et al, J. Biol. Chem. 1996 271 19310-17; Townson et al, Biochem. Biophys. Res. Commun. 1996 220 922-928].

VEGF-B binds specifically to VEGFR-1 [Olofsson B, et al., *Vascular endothelial growth factor B, a novel growth factor for endothelial cells*, Proc Nat'l Acad Sci USA 1996 93(6) 2576-81] and neuropilin-1 [Olofsson B, et al., Vascular Endothelial Growth Factor B (Vegf-B) Binds to Vegf Receptor-1 and Regulates Plasminogen Activator Activity In Endothelial Cells, Proc Nat'l Acad Sci USA, 1998 95(20) 11709-14], a receptor previously identified for collapsins/semaphorins [Soker, S., *Neuropilin in the midst of cell migration and retraction*, Int J Biochem Cell Biol, 2001 33(4) 433-37]. VEGF-B displays a unique expression pattern compared with other VEGF family members, with the highest expression level in the cardiac myocytes [Aase K, et al., *Localization of VEGF-B in the mouse embryo suggests a paracrine role of the growth factor in the developing vasculature*, Developmental Dynamics, 1999 215(1) 12-25], whereas VEGFR-1 is expressed in the adjacent endothelial cells [Aase K, et al., *Localization of VEGF-B in the mouse embryo suggests a paracrine role of the growth factor in the developing vasculature*. Developmental Dynamics, 1999 215 (1) 12-25], and neuropilin-1 (NP-1) is expressed in both endothelium and cardiac myocytes during development [Makinen T, et al., *Differential binding of vascular endothelial growth factor B splice and proteolytic isoforms to neuropilin-1*. Journal of Biological Chemistry, 1999 274(30) 21217-22; and Kitsukawa T, et al., Overexpression of a membrane protein, neuropilin, in chimeric mice causes anomalies in the cardiovascular system, nervous system and limbs, Development, 1995 121(12) 4309-18]. The temporal-spatial expression patterns of VEGF-B and its receptors thus suggest both autocrine and paracrine roles of VEGF-B in the heart [Makinen T, et al., *Differential binding of vascular endothelial growth factor B splice and proteolytic isoforms to neuropilin-1*, J. Biol. Chem. 1999 274(30) 21217-22]. VEGF-B heterodimerizes with VEGF-A when co-expressed [Olofsson B, et al., Vascular endothelial growth factor B, a novel growth factor for endothelial cells, Proc. Nat'l. Acad. Sci. USA 1996 93(6) 2576-81]. Two differently spliced VEGF-B isoforms exist, VEGF-$B_{186}$ and VEGF-$B_{167}$, with the first isoform accounting for about 80% of the total VEGF-B transcripts [Li, X. et al, Growth Factor 2001 19 49-59]. The two polypeptides differ at their carboxy-termini and display different abilities to bind neuropilin-1 [Makinen et al., J. Biol. Chem. 1999 274(30) 21217-22]. Moreover, VEGF-$B_{186}$ is freely secreted, while VEGF-$B_{167}$ is secreted but largely cell-associated, implying that the functional properties of the two proteins may be distinct. Both isoforms bind to extracellular matrix tenascin-X and stimulate endothelial cell proliferation through VEGF-receptor-1 (VEGFR-1) [Ikuta, T., H. Ariga, and K. Matsumoto, Extracellular matrix tenascin-X in combination with vascular endothelial growth factor B enhances endothelial cell proliferation, Genes Cells, 2000 5(11) 913-927].

The capillary density in mice lacking VEGF-B is the same as in normal mice. However, gene targeting studies have shown that VEGF-B deficiency results in an atrial conduction abnormality characterized by a prolonged PQ interval and impaired coronary vasculature [Aase K. et al, Circulation 2001 104 358-64; WO 98/36052; and Bellomo D, et al., *Mice lacking the vascular endothelial growth factor-B gene (Vegfb) have smaller hearts, dysfunctional coronary vasculature, and impaired recovery from cardiac ischemia*. Circulation Research, 2000 86(2) E29-E35]. Thus, accumulating data suggest that VEGF-B has important roles in both physiological and pathological conditions in the cardiovascular system.

VEGF-B may also be involved in tumor development. VEGF-B mRNA can be detected in many tumors and most tumor cell lines [Gunningham, S. P., et al., *VEGF-B expression in human primary breast cancers is associated with lymph node metastasis but not angiogenesis*, J Pathol, 2001 193(3) 325-32; Andre, T., et al., *Vegf, Vegf-B, Vegf-C and their receptors KDR, FLT-1 and FLT-4 during the neoplastic progression of human colonic mucosa*, Int J Cancer, 2000 86(2) 174-81; Eggert, A., et al., *High-level expression of angiogenic factors is associated with advanced tumor stage in human neuroblastomas*, Clin Cancer Res, 2000 6(5) 1900-08; Niki, T., et al., *Expression of vascular endothelial growth factors A, B, C, and D and their relationships to lymph node status in lung adenocarcinoma*, Clin Cancer Res, 2000 6(6) 2431-9; and Salven P, et al., *Vascular Endothelial Growth Factors Vegf-B and Vegf-C Are Expressed In Human Tumors*, Am. J. Pathology, 1998 153(1) 103-108]. VEGF-B expression is especially up-regulated in tumor-associated macrophages in ovarian epithelial tumors [Sowter H., et al., *Expression and Localization Of the Vascular Endothelial Growth Factor Family In Ovarian Epithelial Tumors*, Laboratory Invest. 1997 77(6) 607-14] and renal cell carcinomas [Gunningham, S. P., et al., *Vascular endothelial growth factor-B and vascular endothelial growth factor-C expression in renal cell carcinomas: regulation by the von Hippel-Lindau gene and hypoxia*, Cancer Res, 2001 61(7) 3206-11].

Acute and chronic myocardial ischemia are the leading causes of morbidity and mortality in the industrialized society caused by coronary thrombosis [Varbella, F., et al., *Subacute left ventricular free-wall rupture in early course of acute myocardial infarction. Clinical report of two cases and review of the literature*, G Ital Cardiol, 1999 29(2) 163-70]. Immediately after heart infarction, oxygen starvation causes cell death of the infarcted area, followed by hypertrophy of the remaining viable cardiomyocytes to compensate the need of a normal contractile capacity [Heymans S, et al., *Inhibition of plasminogen activators or matrix metalloproteinases prevents cardiac rupture but impairs therapeutic angiogenesis and causes cardiac failure*, Nat. Med., 1999 5(10) 1135-42]. Prompt post-infarction reperfusion by blood of the infarcted left ventricular wall may significantly reduce the early mortality and subsequent heart failure by preventing apoptosis of the hypertrophied viable myocytes and pathological ventricular remodelling [Dalrymple-Hay, M. J., et al., *Postinfarction ventricular septal rupture: the Wessex experience*, Seminar Thorac Cardiovasc Surg, 1998 10(2) 111-16].

Promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans. The angiogenic process is highly complex and involves the maintenance of the endothelial cells in the cell cycle, degradation of the extracellular matrix, migration and invasion of the surrounding tissue and finally, tube formation. Because of the crucial role of angiogenesis in so many physiological processes, there is a need to develop factors which will promote angiogenesis.

Administration of growth factors such as VEGF-A and FGF-2 has been considered a possible approach for the therapeutic treatment of ischemic heart and limb disorders. However, both animal studies and early clinical trials with VEGF angiogenesis have encountered severe problems [Carmeliet, Nat Med, 2000 6 1102-3; Yancopoulos et al., Nature, 2000 407 242-8; Veikkola et al., Semin Cancer Biol 1999 9 211-20; Dvorak et al., Semin Perinatol 2000 24 75-8; Lee et al., Circulation, 2000 102 898-901]. VEGF-A stimulated microvessels are disorganized, sinusoidal and dilated, much like those found in tumors [Lee et al., Circulation 2000 102 898-901; and Springer et al., Mol. Cell 1998 2 549-559]. Moreover, these vessels are usually leaky, poorly perfused, torturous and likely to rupture and regress. Thus, these vessels have limited ability to improve the ischemic conditions of myocardium. In addition, the leakage of blood vessels induced by VEGF-A (also known as Vascular Permeability Factor) could cause cardiac edema that leads to heart failure. Unregulated VEGF-A expression in the myocardium also could lead to the development of hemangioma or the growth of micrometastases in distal organs instead of functional vessels.

Thus, despite some advances in clinical treatment and prevention which have been achieved in the prior art, insufficient or abnormal post-infarction revascularization remains a major cause of the death of the otherwise viable myocardium and leads to progressive infarct extension and fibrous replacement, and ultimately heart failure. Therefore, therapeutic agents promoting normal post-infarction revascularization with minimal toxicity are still needed and there is an ongoing requirement for new angiogenic factors and new methods of angiogenic therapy.

SUMMARY OF THE INVENTION

It is an object of the invention to provide a new method of stimulating and/or promoting revascularization of heart muscle following coronary infarction.

It is also an object of the invention to provide a method of treating an ischemic condition or circulatory insufficiency in a mammal by stimulating or promoting vasculogenesis.

These and other objects are achieved in accordance with a first aspect of the invention by providing a method for promoting vascularization of tissue in an organism, comprising administering to said organism in need of such treatment an effective amount of VEGF-B, or a fragment or analog thereof having the biological activity of VEGF-B.

In another aspect of the invention, the objects are achieved by providing a method of stimulating vascularization of ischemic tissue by angiogenesis, comprising the step of administering an effective angiogenesis stimulating amount of VEGF-B or a fragment or analog thereof having vascularization stimulating activity.

In accordance with a further aspect of the invention, the objects are achieved by providing a method of stimulating arteriogenesis or expansion of pre-existing muscularized arteries, i.e. collateral blood vessels.

The objects of the invention are also achieved in accordance with yet another aspect of the invention by providing a method of stimulating vascularization in a mammal in need thereof, comprising administering to said mammal a therapeutically effective amount of VEGF-B or a fragment or analog thereof having angiogenesis stimulating activity.

As used herein, the term "vascularization" is used in a generic sense embracing the generation of new blood vessels or expansion of existing blood vessels whether by capillary angiogenesis or by arteriogenesis, or both.

The ischemic disease state following infarction is due to imparied perfusion as a consequence of the reduced blood flow. The problems can be alleviated by reperfusing the infarction area with blood. Because most blood vessels and cardiomyocytes in the infarction area will die and be replaced with fibroblasts to form scar tissue, this can only be achieved by an increase of the blood flow which is dependent upon new vessels in the infarction area. Accordingly, effective revascularization of the infarcted heart muscle may significantly reduce the early mortality and subsequent heart failure by preventing apoptosis etc.

Candidate conditions for vasculogenic or angiogenic treatment with VEGF-B thus include, inter alia, (1) patients with chronic stable angina due to angiographically documented coronary artery disease [Carmeliet P and Collen D, *Transgenic mouse models in angiogenesis and cardiovascular disease* [Review], J. Pathology, 2000 190(3) 387-405]; (2) patients with critical limb ischemia or chronic venous leg ulcerations; (3) patients suffering from diabetic neuropathy [Schratzberger, P., et al., *Reversal of experimental diabetic neuropathy by VEGF gene transfer*. J Clin Invest, 2001 107 (9) 1083-92; and Schratzberger, P., et al., *Favorable effect of VEGF gene transfer on ischemic peripheral neuropathy*, Nat Med, 2000 6(4) 405-13.]; (4) patients with postnatal arterial insufficiency; (5) patients with post-balloon-angioplasty restenosis [Carmeliet P, Moons L, and Collen D, MOUSE MODELS OF ANGIOGENESIS, ARTERIAL STENOSIS, ATHEROSCLEROSIS AND HEMOSTASIS [Review], Cardiovas Res, 1998 39(1) 8-33; and Baumgartner, I. and Isner, J. M., *Somatic gene therapy in the cardiovascular system*, Annu Rev Physiol, 2001 63 427-50]; (6) patients with ischemic cardiovascular disease [Carmeliet P, et al., *Impaired myocardial angiogenesis and ischemic cardiomyopathy in mice lacking the vascular endothelial growth factor isoforms VEGF(164) and VEGF(188)*, Nat Med, 1999 5(5) 495-502; and Simons, M., et al., *Clinical trials in coronary angiogenesis: issues, problems, consensus: An expert panel summary*, Circulation, 2000 102(11) E73-86] and (7) patients with end-stage coronary artery disease [Laham, R J, Simons, M and Sellke, F, *Gene transfer for angiogenesis in coronary artery disease*, Annu Rev Med, 2001 52 485-502].

In accordance with the invention, there are numerous techniques which can be used to administer an effective vasculogenesis promoting or angiogenesis stimulating amount of VEGF-B to a patient suffering from ischemia or some other condition which may be alleviated by vasculogenesis or angiogenesis. VEGF-B administration may be effected either as recombinant protein or by gene transfer either as naked DNA or in a vector [Kornowski R, Fuchs S, Leon M B, Epstein S E, *Delivery strategies to achieve therapeutic myocardial angiogenesis*, Circulation, 2000 101(4) 454-8; Simons M, Bonow R O, Chronos N A, Cohen D J, Giordano F J, Hammond H K, et al., *Clinical trials in coronary angiogenesis: issues, problems, consensus: An expert panel summary*, Circulation, 2000 102(11) E73-86; and Isner J M, Asahara T, *Angiogenesis and vasculogenesis as therapeutic strategies for postnatal neovascularization*, J Clin Invest, 1999 103 (9) 1231-36]. If desired, regulatable vectors may be used as described in Ozawa et al, Annu Rev Pharmacol. & Toxicol, 2000 40 295-317.

For example, VEGF-B can be administered by direct myocardial injection of naked plasmid DNA encoding VEGF-B during surgery in patients with chronic myocardial ischemia following procedures outlined in Vale, P. R., et al., *Left ventricular electromechanical mapping to assess efficacy of phVEGF(165) gene transfer for therapeutic angiogenesis in chronic myocardial ischemia*, Circulation, 2000 102 965-74.

VEGF-B can also be administered by direct myocardial injection of VEGF-B protein via a minithoracotomy. Preferably, it is given as a bolus dose of from 1 µg/kg to 15 mg/kg, preferably between 5 µg/kg and 5 mg/kg, and most preferably between 0.2 and 2 mg/kg. Continuous infusion may also be used, for example, by means of an osmotic minipump as described in Heyman et al., Nat Med, 1999 5 1135-152. If so, the medicament may be infused at a dose between 5 and 20 µg/kg/minute, preferably between 7 and 15 µg/kg/minute.

Alternatively VEGF-B can be administered by catheter-based myocardial VEGF-B gene transfer. In this technique, a steerable, deflectable 8F catheter incorporating a 27-guage needle is advanced percutaneously to the left ventricular myocardium. A total dose of 200 µg/kg is administered as 6 injections into the ischemic myocardium (total, 6.0 mL). Injections are guided by NOGA left ventricular electromechanical mapping. See Vale, P. R., et al., *Randomized, single-blind, placebo-controlled pilot study of catheter-based myocardial gene transfer for therapeutic angiogenesis using left ventricular electro-mechanical mapping in patients with chronic myocardial ischemia*, Circulation, 2001 103(17) 2138-43.

Another possibility for VEGF-B administration is injection of VEGF-B plasmid in the muscles of an ischemic limb in accordance with procedures described in Simovic, D., et al., *Improvement in chronic ischemic neuropathy after intramuscular phVEGF165 gene transfer in patients with critical limb ischemia*, Arch Neurol, 2001 58(5) 761-68.

Still another technique for effective VEGF-B administration is by intra-arterial gene transfer of the VEGF-B gene using adenovirus and replication defective retroviruses as described in Baumgartner I and Isner J M, *Somatic gene therapy in the cardiovascular system*, Annu Rev Physiol, 2001 63 427-50.

An additional possibility for administering VEGF-B is by intracoronary and intravenous administration of recombinant VEGF-B protein following procedures described in Post, M. J., et al., *Therapeutic angiogenesis in cardiology using protein formulations*, Cardiovasc Res, 2001 49 522-31.

A still further possibility is to use ex vivo expanded endothelial progenitor cells (EPCs) engineered to express VEGF-B for myocardial neovascularization as described in Kawamoto, A., et al., *Therapeutic potential of ex vivo expanded endothelial progenitor cells for myocardial ischemia*. Circulation, 2001 103(5) 634-37.

Yet another technique which may be used to administer VEGF-B is percutaneous adenovirus-mediated VEGF-B gene delivery to the arterial wall in injured atheromatous stented arteries. See, for example, Maillard, L., et al., *Effect of percutaneous adenovirus-mediated Gax gene delivery to the arterial wall in double-injured atheromatous stented rabbit iliac arteries*, Gene Ther, 2000 7(16) 1353-61; and Laham R J, Simons M, and Sellke F, *Gene transfer for angiogenesis in coronary artery disease*, Annu Rev Med, 2001 52 485-502.

In one advantageous aspect of the invention, a therapeutically effective dose of VEGF-B is administered by bolus injection of the active substance into ischemic tissue, e.g. heart or peripheral muscle tissue. The effective dose will vary depending on the weight and condition of the ischemic subject and the nature of the ischemic condition to be treated. It is considered to be within the skill of the art to determine the appropriate dosage for a given subject and condition.

In accordance with another aspect of the invention, VEGF-B is administered by continuous delivery, e.g., using an osmotic minipump, until the patient is able to self-maintain a functional vascular network.

In another advantageous aspect within the scope of the invention, VEGF-B is effectively administered to an ischemic subject by contacting ischemic tissue with a viral vector, e.g. an adenovirus vector, containing a polynucleotide sequence encoding VEGF-B operatively linked to a promoter sequence.

VEGF-B may also be effectively administered by implantation of a micropellet impregnated with active substance in the direct vicinity of ischemic tissue.

If desired, the VEGF-B may be co-administered with at least one additional growth factor selected from the group consisting of VEGF-A, VEGF-C, VEGF-D, PlGF, PDGF-A, PDGF-B, PDGF-C, PDGF-D and FGF.

The active VEGF-B substance may comprise the VEGF-$B_{167}$ and/or VEGF-$B_{186}$ isoforms or a fragment or analog thereof having the ability to stimulate and/or promote revascularization, angiogenesis and/or arteriogenesis [Olofsson B, et al., *Vascular Endothelial Growth Factor B (Vegf-B) Binds to Vegf Receptor-1 and Regulates Plasminogen Activator Activity In Endothelial Cells*, Proc Nat'l Acad Sci USA, 1998 95(20) 11709-14]. Active analogs should exhibit at least 85% sequence identity, preferably at least 90% sequence identity, particularly preferably at least 95% sequence identity, and especially preferably at least 98% sequence identity to the natural VEGF-B polypeptides, as determined by BLAST analysis.

As used herein, the term "VEGF-B protein" collectively refers to the known VEGF-$B_{167}$ and VEGF-$B_{186}$ polypeptide isoforms as well as to fragments or analogs thereof which have the vasculogenesis stimulating activity of VEGF-B, and to polynucleotides which encode VEGF-B, or a fragment or analog thereof having vasculogensis stimulating activity. The polynucleotide can be naked or in a vector or liposome. The active substance typically will include the amino acid sequence Pro-Xaa-Cys-Val-Xaa-Xaa-Xaa-Arg-Cys-Xaa-Gly-Cys-Cys (where Xaa may be any amino acid) which is characteristic of VEGF-B.

Polypeptides comprising conservative substitutions, insertions, or deletions, but which still retain the biological activity of VEGF-B are clearly to be understood to be within the scope of the invention. Persons skilled in the art will be well aware of methods which can readily be used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analog may retain the required aspects of the biological activity of VEGF-B. Such compounds can readily be made and tested by methods known in the art, and are also within the scope of the invention.

In addition, possible variant forms of the VEGF-B polypeptide which may result from alternative splicing, as are known to occur with VEGF-A and VEGF-B, and naturally-occurring allelic variants of the nucleic acid sequence encoding VEGF-B are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

Such variant forms of VEGF-B can be prepared by targeting non-essential regions of the VEGF-B polypeptide for modification. These non-essential regions are expected to fall outside the strongly-conserved regions of the VEGF/PDGF family of growth factors. In particular, the growth factors of the VEGF family, including VEGF-B, are dimeric, and VEGF-A, VEGF-B, VEGF-C, VEGF-D, PlGF, PDGF-A and PDGF-B show complete conservation of eight cysteine residues in the N-terminal domains, i.e. the PDGF/VEGF-like domains [Olofsson et al., Proc Natl Acad Sci USA, 1996 93 2576-2581; Joukov et al., EMBO J., 1996 15 290-298]. These cysteines are thought to be involved in intra- and inter-molecular disulfide bonding. In addition there are further strongly, but not completely, conserved cysteine residues in the C-terminal domains. Loops 1, 2 and 3 of each subunit, which are formed by intra-molecular disulfide bonding, are involved in binding to the receptors for the PDGF/VEGF family of growth factors [Andersson et al, Growth Factors, 1995 12 159-64].

Persons skilled in the art thus are well aware that in most cases these cysteine residues should be preserved in any proposed variant form, although there may be exceptions since receptor-binding VEGF-B analogs are known in which one or more of the cysteines is not conserved. Similarly, a skilled worker would be aware that the active sites present in loops 1, 2 and 3 also should be preserved. Other regions of the molecule can be expected to be of lesser importance for biological function, and therefore offer suitable targets for modification. Modified polypeptides can readily be tested for their ability to show the biological activity of VEGF-B by routine activity assay procedures such as the endothelial cell proliferation assay.

In a variation of the invention, a proteolytic site is inserted between an activated monomer of VEGF-A, VEGF-B, VEGF-C, VEGF-D, VEGF-B, PDGF-A, PDGF-B, PDGF-C, PDGF-D or PlGF and a mutant CUB domain linkage which is dimerized to an activated monomer of VEGF-A, VEGF-B, VEGF-C, VEGF-D, PDGF-A, PDGF-B, PDGF-C, PDGF-D or PlGF and renders the monomer temporarily inactive. An addition of the specific protease(s) for this proteolytic site would cleave the CUB domain and thereby release an activated dimer that can then bind to its corresponding receptor. In this way, a controlled release of an activated dimer is made possible.

Preferably where amino acid substitution is used, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

| Conservative Substitutions I | |
|---|---|
| SIDE CHAIN CHARACTERISTIC | AMINO ACID |
| Aliphatic | |
| Non-polar | G A P |
|  | I L V |
| Polar - uncharged | C S T M |
|  | N Q |
| Polar - charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp. 71-77] as set out in the following Table B.

TABLE B

| Conservative Substitutions II | |
|---|---|
| SIDE CHAIN CHARACTERISTIC | AMINO ACID |
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions also are set out in the following Table C.

TABLE C

| Conservative Substitutions III | |
|---|---|
| Original Residue | Exemplary Substitution |
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |

TABLE C-continued

| Conservative Substitutions III | |
|---|---|
| Original Residue | Exemplary Substitution |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the VEGF-B proteins of the invention can be modified, for instance, by glycosylation, amidation, carboxylation, or phosphorylation, or by the creation of acid addition salts, amides, esters, in particular C-terminal esters, and N-acyl derivatives of the peptides of the invention. The proteins also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

In particular, it is anticipated that the VEGF-B proteins can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin).

Examples of VEGF-B analogs are described in WO 98/28621 and in Olofsson et al., Proc. Nat'l. Acad. Sci. USA, 1998 95 11709-11714, which are incorporated herein by reference.

Clinical applications of the invention include diagnostic applications, acceleration of angiogenesis in tissue or organ transplantation, or stimulation of wound healing, or connective tissue development, or to establish collateral circulation in tissue infarction or arterial stenosis, such as coronary artery disease.

The absence of serious adverse effects from VEGF-B administration is indicated by the fact that transgenic mice which overexpress VEGF-B under different promoters do not display any overt abnormalities. From this it may be concluded that minimal side effects can be expected in therapeutic administration of VEGF-B. In consequence of its lack of adverse side effects, VEGF-B may be appropriately administered at very early stages of ischemic conditions.

BRIEF DESCRIPTION OF THE DRAWINGS

The invention will be described in further detail hereinafter with reference to experiments demonstrating the activity of VEGF-B in promoting vascularization of ischemic heart muscle, the results of which are shown in the accompanying drawing figures in which.

DETAILED DESCRIPTION

Example 1

Role of VEGF-B in Revascularization After Heart Infarction

Procedure

Chronic myocardial ischemia is achieved by ligation of the left anterior descending (LAD) coronary artery using 8 weeks old normal and VEGF-B deficient mice after anaesthesia. The VEGF-B deficient mice are described in published international application no. WO 98/36052. Prior to challenge, the capillary densities of both wild type (normal) and knock out (VEGF-B deficient) were the same. Seven days after LAD ligation, infarcted hearts were fixed and collected. The infarcted hearts were sectioned longitudinally (6 m). Heamatoxylin & eosin and immunohistochemistry staining were performed using thrombomodulin for endothelial cells and smooth muscle alpha-actin for smooth muscle cells as markers. Antibodies to thrombomodulin were obtained from Dr. Ed Conway of Leuven University in Belgium. Antibodies to smooth muscle cell alpha actin were obtained commercially (DAKO, X0910, Denmark). Infarcted area and vessel densities were calculated using a Quantinet Q600 image analysis system (Leica, Brussels, Belgium). Data were analysed using the Student T test.

Results

Seven days after LAD artery ligation, vessel densities in the infarcted area were calculated using thrombomodulin (TM) and smooth muscle cell alpha-actin (SMC) as markers. The results are illustrated in FIGS. 1(a) and (b) and 3(a) and (b), respectively, and tabulated graphically in FIGS. 2 and 4.

Figure 1A:
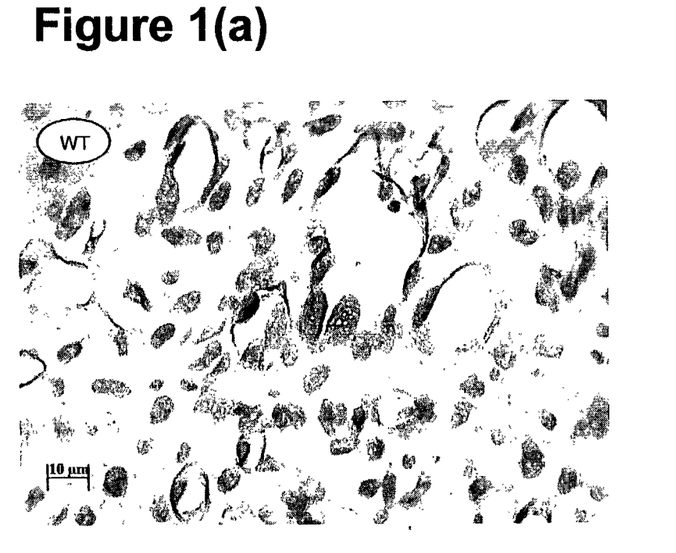
FIGS. 1(a) and (b) are microphotographs showing post-infarction revascularization in mouse hearts visualized by thrombomodulin staining in wild type (WT) and VEGF-B deficient (KO) mice, respectively.
Figure 1B:
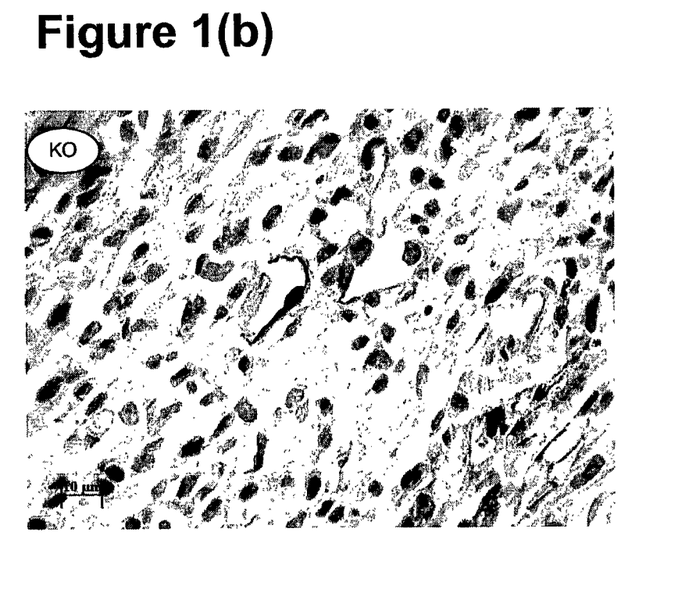

FIG. 1(a) and (b) show thrombomodulin staining in wild type (WT) and VEGF-B deficient (KO) hearts after infarction. The endothelium cell marker, thrombomodulin stains endothelium cells lining the lumen of vessels. In the infarcted area of the wild type heart (WT), there are more positive staining of different sized vessels compared with that of the VEGF-B deficient one (KO).

Figure 2:
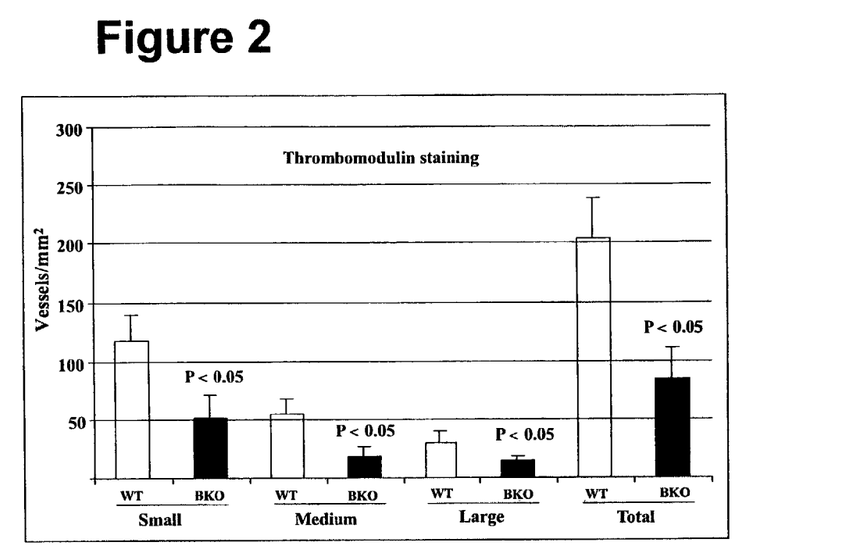
FIG. 2 is a graphic representation of the revascularization vessel densities in the infarcted areas in normal (WT) and VEGF-B deficient (KO) mice from FIGS. 1(a) and (b).

As can be seen from FIG. 2, using thrombomodulin as the marker, total vessel density in the VEGF-B deficient mice was about 63% of that of the normal mice on average (P<0.01, n=9). When the vessels were classified into three different groups, large, medium-sized and small vessels, results showed the same deficiency in all the groups (VEGF-B deficient mice: 18.6±3.1 large vessels/mm$^2$, 34.8±8.5 medium-sized vessels/mm$^2$, 75±20.3 small vessels/mm$^2$; normal mice: 30.6±8.5 large vessels/mm$^2$, 54.9±13.4 medium-sized vessels/mm$^2$, 117.7±20.8 small vessels/mm$^2$, n=9 each group, P<0.05 in all the groups).

Figure 3A:
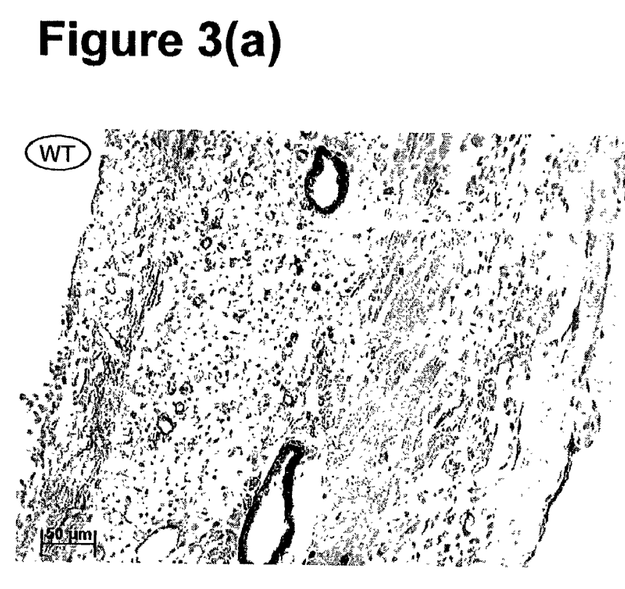
FIGS. 3(a) and (b) a microphotographs showing post-infarction revascularization in mouse hearts visualized by smooth muscle alpha-actin staining in wild type (WT) and VEGF-B deficient (KO) mice, respectively.
Figure 3B:
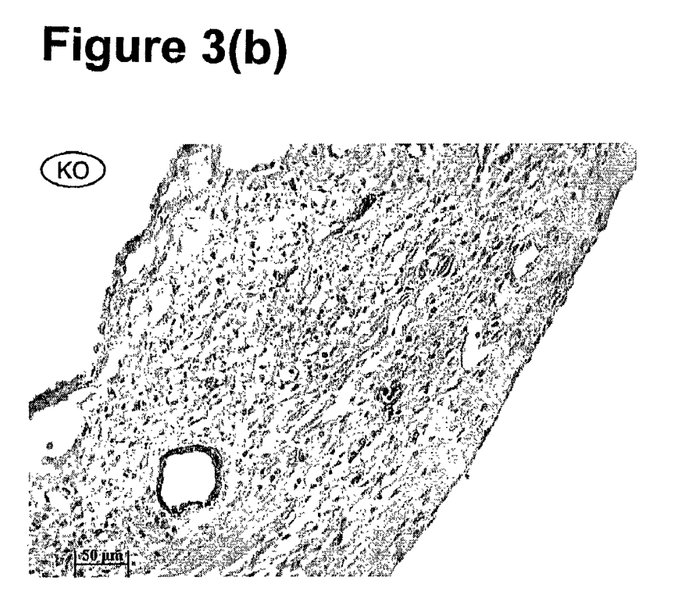

FIGS. 3(a) and (b) show the results of smooth muscle cell alpha actin staining in wild type (WT) and VEGF-B deficient (KO) hearts after infarction. The smooth muscle cell marker, smooth muscle cell alpha actin, stains smooth muscle cells surrounding the vessels. In the infarcted area of the wild type heart (WT), there are more positive staining of different sized vessels compared with those in the VEGF-B deficient heart (KO).

Figure 4:
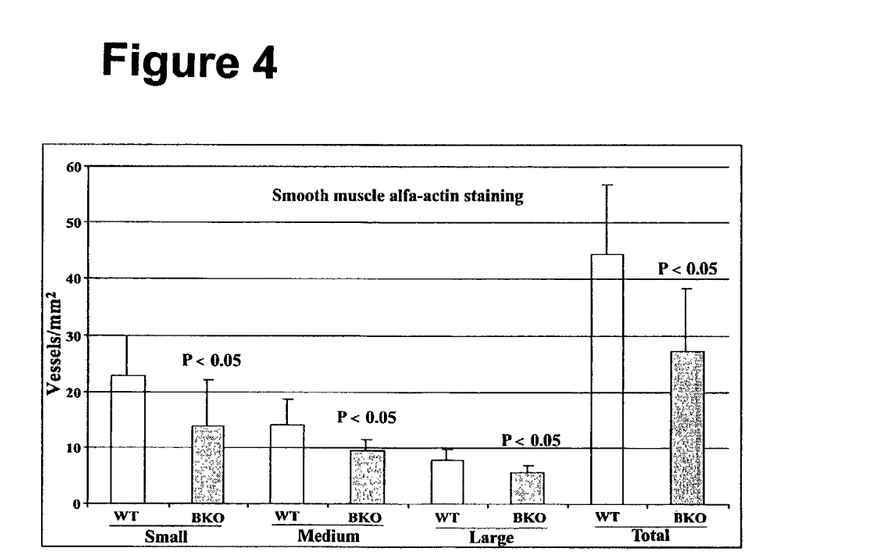
FIG. 4 is a graphic representation of the revascularization vessel densities in the infarcted areas in normal (WT) and VEGF-B deficient (KO) mice from FIGS. 3(a) and (b).

As can be seen from the graph in FIG. 4, when tissue sections were stained with smooth muscle alpha-actin for vascular smooth muscle cells, the VEGF-B deficient mice showed the same revascularization defect after heart infarction observed in the previous test. The VEGF-B deficient animals displayed only 61% of the normal vessel density in total (P<0.05, n=9). Vessels in different sizes showed the same result (VEGF-B deficient mice: 5.5±1.3 large vessels/mm$^2$, 8.0±2.0 medium-sized vessels/mm$^2$, 13.8±8.3 small vessels/mm$^2$; normal mice: 7.7±1.9 large vessels/mm$^2$, 14.0±4.8 medium-sized vessels/mm$^2$, 22.7±7.2 small vessels/mm$^2$, n=9 each group, P<0.05 in all the groups).

Thus, the test data clearly demonstrates that VEGF-B deficiency leads to impaired revascularization after heart infarction. It follows that the presence of VEGF-B is necessary for revascularization after heart infarction and that in cases of cardiac ischemia, administration of a therapeutically effective amount of VEGF-B may stimulate or promote compensatory vascular development.

Example 2

Angiogenic Activity of VEGF-B

The angiogenic activity of VEGF-B is tested using the mouse cornea model and in the avian chorioallantoic membrane tests following the procedure described in Cao et al., *Proc. Natl. Acad. Sci. USA* 95: 14389-14394, 1998.

Example 3

Induction of Angiogenesis by VEGF-B

The ability of VEGF-B to induce angiogenesis in ischemic tissue is tested following the procedure described in Witzenbichler et al., *Am. J. Pathol.* 153: 381-394, 1998.

Example 4

Generation of a Recombinant Adenoviral Vector Comprising VEGF-B

The cDNA encoding human VEGF-B$_{167}$ was cloned between the strong enhancer/promoter of the cytomegalovirus (CMV) immediate early genes and the SV40 polyadenylation signal of the bacterial plasmid pACCMVpLpA (Gomez-Foix A. et al. (1992) *J. Biol. Chem.* 267, 25129 and Janssens S. P. et al. (1996) *J. Clin. Invest.* 98(2)317). The plasmid also contained E1A-deleted sequences of type 5 adenovirus including the origin of replication, the packaging signal and a polylinker. Recombinant adenovirus was generated through homologous recombination with pJM17, a bacterial plasmid containing the full-length adenoviral genome, following cotransfection in E1A-transformed human embryonic retinal (911) cells. The presence of VEGF-B cDNA in virion DNA isolated from infected 911 cells was confirmed by PCR analysis. Viral isolates containing VEGF-B (AdCM-V.VEGF-B) were amplified on confluent 911 cells and, after appearance of cytopathic effects, isolated, precipitated, and concentrated by discontinuous CsCl gradient. Viral titers were determined by infection of monolayers of 911 cells with serial dilutions of the recombinant adenovirus. For in vivo studies, $3\times10^9$ plaque forming units (pfu) VEGF-B or control RR5 adenovirus were injected intravenously per mouse.

Example 5

Induction of Angiogenesis by Adenoviral VEGF-B Gene Transfer

Wild-type (WT) mice were subjected to ligation of the left descendens coronary artery as described above under Example 1 to induce myocardial ischemia. Thereafter, a group of eleven test animals were treated intravenously with $3\times10^9$ pfu AdCMV.hVEGF-B from Example 4 per mouse. As a negative control, another group of 13 animals was treated with $3\times10^9$ pfu of AdRR5 virus per mouse. Revascularization of infarcts was measured by counting the number of vessels per $mm^2$ of infarct area within seven days after ligation of the coronary artery. Results are shown in the following Table 1:

TABLE 1

| | Virus | Dose | Results vessels per $mm^2$ |
|---|---|---|---|
| Invention | AdVEGF-B | $3 \times 10^9$ pfu/mouse | $246 \pm 11.5$ (p = 0.0035) |
| Control | AdRR5 | $3 \times 10^9$ pfu/mouse | $193 \pm 12$ |

The results clearly demonstrate that the gene therapy treatment with VEGF-B DNA in a viral vector resulted in increased re-vascularization of the infarct area compared to the negative control.

Example 6

Induction of Angiogenesis by Administration of Recombinant VEGF-B

Wild-type (WT) mice were subjected to ligation of the left descendens coronary artery as described above under Example 1 to induce myocardial ischemia. A group of five ischemic test animals was thereafter treated with a solution containing recombinant human $VEGF-B_{167}$ (r $VEGF-B_{167}$) supplied by Amrad Corporation Limited of Melbourne, Australia. The solution containing recombinant human VEGF-B was administered via an osmotic minipump implanted subcutaneously on the back of each mouse. The protein leaks out into the extracellular space and is resorbed in the blood. The recombinant VEGF-B was administered at a rate of 10 micrograms of active substance per mouse per week. As a negative control a second group of five animals was treated with an identical amount of physiological saline solution. Revascularization of infarcts was measured by counting the number of vessels per $mm^2$ of infarct area within seven days after ligation of the coronary artery. Results are shown in the following Table 2:

TABLE 2

| | Treatment | Dose | Results vessels per $mm^2$ |
|---|---|---|---|
| Invention | r $VEGF-B_{167}$ | 10 µg/week | $285 \pm 33$ (p = 0,045) |
| Control | saline solution | equivalent volume | $194 \pm 17$ |

The results clearly show that administration of recombinant VEGF-B167 resulted in increased re-vascularization of the infarct area compared to the negative control.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

REFERENCES

1. Carmeliet, P., *Mechanisms of angiogenesis and arteriogenesis*. Nat Med, 2000. 6(4): p. 389-95.
2. Carmeliet, P. and R. K. Jain, *Angiogenesis in cancer and other diseases*. Nature, 2000. 407(6801): p. 249-57.
3. Li, X. and U. Eriksson, *Novel VEGF family members: VEGF-B, VEGF-C and VEGF-D*. Int J Biochem Cell Biol, 2001. 33(4): p. 421-6.
4. Carmeliet P, et al., *Abnormal blood vessel development and lethality in embryos lacking a single VEGF allele*. Nature, 1996. 380(6573): p. 435-9.
5. Ferrara N, et al., *Heterozygous embryonic lethality induced by targeted inactivation of the VEGF gene*. Nature, 1996. 380(6573): p. 439-42.
6. Poltorak, Z., T. Cohen, and G. Neufeld, *The VEGF splice variants: properties, receptors, and usage for the treatment of ischemic diseases*. Herz, 2000. 25(2): p. 126-9.
7. Carmeliet, P., *VEGF gene therapy: stimulating angiogenesis or angioma-genesis?* [In Process Citation]. Nat Med, 2000. 6(10): p. 1102-3.
8. Olofsson B, et al., *Vascular endothelial growth factor B, a novel growth factor for endothelial cells*. Proceedings of the National Academy of Sciences of the United States of America, 1996. 93(6): p. 2576-81.
9. Grimmond S, et al., *Cloning and characterization of a novel human gene related to vascular endothelial growth factor*. Genome Research, 1996. 6(2): p. 124-31.
10. Olofsson B, et al., *Vascular Endothelial Growth Factor B (Vegf-B) Binds to Vegf Receptor-1 and Regulates Plasminogen Activator Activity In Endothelial Cells*. Proceedings of the National Academy of Sciences of the United States of America, 1998. 95(20): p. 11709-11714.
11. Soker, S., *Neuropilin in the midst of cell migration and retraction*. Int J Biochem Cell Biol, 2001. 33(4): p. 433-7.
12. Aase K, et al., *Localization of VEGF-B in the mouse embryo suggests a paracrine role of the growth factor in the developing vasculature*. Developmental Dynamics, 1999. 215(1): p. 12-25.
13. Makinen T, et al., *Differential binding of vascular endothelial growth factor B splice and proteolytic isoforms to neuropilin-1*. Journal of Biological Chemistry, 1999. 274 (30): p. 21217-21222.
14. Kitsukawa T, et al., *Overexpression of a membrane protein, neuropilin, in chimeric mice causes anomalies in the cardiovascular system, nervous system and limbs*. Development, 1995. 121(12): p. 4309-18.
15. Ikuta, T., H. Ariga, and K. Matsumoto, *Extracellular matrix tenascin-X in combination with vascular endothelial growth factor B enhances endothelial cell proliferation*. Genes Cells, 2000. 5(11): p. 913-927.
16. Bellomo D, et al., *Mice lacking the vascular endothelial growth factor-B gene (Vegfb) have smaller hearts, dysfunctional coronary vasculature, and impaired recovery from cardiac ischemia*. Circulation Research, 2000. 86(2): p. E29-E35.

17. Gunningham, S. P., et al., *VEGF-B expression in human primary breast cancers is associated with lymph node metastasis but not angiogenesis.* J Pathol, 2001. 193(3): p. 325-32.

18. Andre, T., et al., *Vegf, Vegf-B, Vegf-C and their receptors KDR, FLT-1 and FLT-4 during the neoplastic progression of human colonic mucosa.* Int J Cancer, 2000. 86(2): p. 174-81.

19. Eggert, A., et al., *High-level expression of angiogenic factors is associated with advanced tumor stage in human neuroblastomas* [In Process Citation]. Clin Cancer Res, 2000. 6(5): p. 1900-8.

20. Niki, T., et al., *Expression of vascular endothelial growth factors A, B, C, and D and their relationships to lymph node status in lung adenocarcinoma* [In Process Citation]. Clin Cancer Res, 2000. 6(6): p. 2431-9.

21. Salven P, et al., *Vascular Endothelial Growth Factors Vegf-B and Vegf-C Are Expressed In Human Tumors.* American Journal of Pathology, 1998. 153(1): p. 103-108.

22. Sowter Hm, et al., *Expression and Localization Of the Vascular Endothelial Growth Factor Family In Ovarian Epithelial Tumors.* Laboratory Investigation, 1997. 77(6): p. 607-614.

23. Gunningham, S. P., et al., *Vascular endothelial growth factor-B and vascular endothelial growth factor-C expression in renal cell carcinomas: regulation by the von Hippel-Lindau gene and hypoxia.* Cancer Res, 2001. 61(7): p. 3206-11.

24. Varbella, F., et al., *Subacute left ventricular free-wall rupture in early course of acute myocardial infarction. Clinical report of two cases and review of the literature.* G Ital Cardiol, 1999. 29(2): p. 163-70.

25. Heymans S, et al., *Inhibition of plasminogen activators or matrix metalloproteinases prevents cardiac rupture but impairs therapeutic angiogenesis and causes cardiac failure.* Nature Medicine, 1999. 5(10): p. 1135-1142.

26. Dalrymple-Hay, M. J., et al., *Postinfarction ventricular septal rupture: the Wessex experience.* Semin Thorac Cardiovasc Surg, 1998. 10(2): p. 111-6.

What is claimed is:

1. A method of promoting vascularization of heart tissue in a mammal in need thereof comprising administering to the mammal an effective amount of a polynucleotide encoding VEGF-$B_{186}$ protein, wherein said polynucleotide is operatively linked to a suitable promoter sequence and is administered to the site where vascularization is desired.

2. A method according to claim 1, wherein the polynucleotide is administered by direct injection of naked DNA.

3. A method according to claim 1, wherein the polynucleotide is administered by injection of a plasmid vector containing the polynucleotide.

4. A method according to claim 1, wherein polynucleotide is administered by introduction of ex vivo expanded endothelial progenitor cells engineered to express a VEGF-$B_{186}$ protein.

5. A method according to claim 1, wherein the polynucleotide is administered by percutaneous adenovirus-mediated delivery to an injured arterial wall.

6. A method according to claim 1, wherein the polynucleotide is administered by intra-arterial gene transfer using an adenovirus vector or a replication defective retrovirus vector.

7. A method according to claim 1, wherein the polynucleotide is administered by myocardial injection.

8. A method according to claim 1, wherein the polynucleotide is administered by direct injection into a muscle of an ischemic heart.

9. A method according to claim 1, wherein the polynucleotide is a viral vector.

10. The method according to claim 1, wherein vascularization of ischemic heart tissue is promoted.

11. The method according to claim 1, wherein the polynucleotide is delivered by an adenoviral vector.

* * * * *